United States Patent
Clarke et al.

(10) Patent No.: US 9,480,597 B2
(45) Date of Patent: Nov. 1, 2016

(54) APPARATUS FOR INTRAOCULAR INJECTION

(71) Applicant: SANOFI-AVENTIS DEUTSCHLAND GMBH, Frankfurt am Main (DE)

(72) Inventors: Alastair Robert Clarke, Cheshire (GB); David Heighton, Fife (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 255 days.

(21) Appl. No.: 14/349,317

(22) PCT Filed: Sep. 17, 2012

(86) PCT No.: PCT/EP2012/068238
§ 371 (c)(1),
(2) Date: Apr. 2, 2014

(87) PCT Pub. No.: WO2013/050236
PCT Pub. Date: Apr. 11, 2013

(65) Prior Publication Data
US 2014/0257207 A1   Sep. 11, 2014

(30) Foreign Application Priority Data
Oct. 7, 2011 (EP) .................. 11184406

(51) Int. Cl.
*A61F 9/00* (2006.01)
*A61M 5/32* (2006.01)

(52) U.S. Cl.
CPC .......... *A61F 9/0017* (2013.01); *A61M 5/3202* (2013.01); *A61M 5/3216* (2013.01)

(58) Field of Classification Search
CPC ............. A61F 9/0017; A61M 5/3202; A61M 5/3216; A61M 5/3204; A61M 2025/0175; A61M 39/06; A61M 2039/0633; A61M 2039/064; A61M 2039/0666; A61M 2039/0673; A61M 2039/2433; A61M 2039/244; A61M 2039/2473; A61M 2039/267–2039/268
See application file for complete search history.

(56) References Cited

U.S. PATENT DOCUMENTS

2005/0033234 A1* 2/2005 Sadowski ........... A61M 5/2033
                                                                  604/140
2009/0259195 A1* 10/2009 Lin Lee .................. A61M 5/24
                                                                  604/195

FOREIGN PATENT DOCUMENTS

| EP | 2189173 | 5/2010 |
|----|---------|--------|
| FR | 2799977 | 4/2001 |
| WO | 2008/097072 | 8/2008 |

OTHER PUBLICATIONS

International Preliminary Report on Patentability for Int. App. No. PCT/EP2012/068238, mailed Apr. 17, 2014.
International Search Report and Written Opinion for Int. App. No. PCT/EP2012/068238, mailed Nov. 26, 2012.

* cited by examiner

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

Described is an apparatus for intraocular injection comprising a body adapted to accommodate a syringe having a needle, an outer sleeve telescopically coupled to the body, and at least two arms hingedly coupled to the outer sleeve. Each of the arms comprises a medial portion adapted to encase at least a portion of the needle. When the body moves distally relative 10 to said outer sleeve, the body engages the arms separating the medial portions.

7 Claims, 3 Drawing Sheets

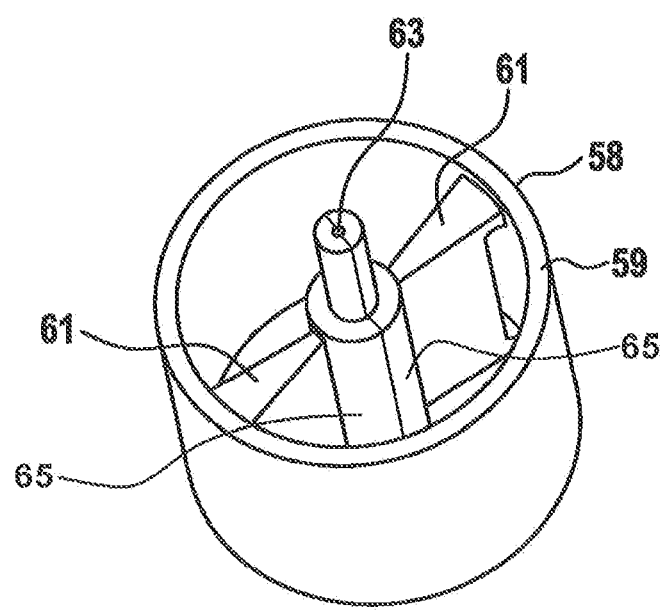
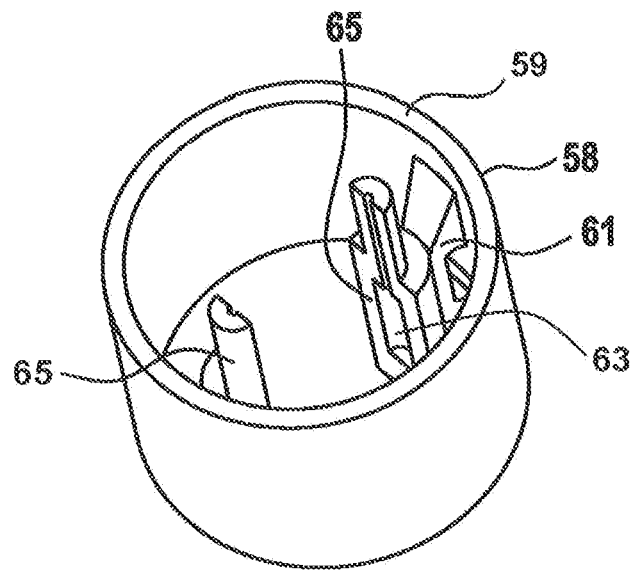

APPARATUS FOR INTRAOCULAR INJECTION

CROSS REFERENCE TO RELATED APPLICATIONS

The present application is a U.S. National Phase Application pursuant to 35 U.S.C. §371 of International Application No. PCT/EP2012/068238 filed Sep. 17, 2012, which claims priority to European Patent Application No. 11184406.4 filed Oct. 7, 2011. The entire disclosure contents of these applications are herewith incorporated by reference into the present application.

TECHNICAL FIELD

The present invention relates to an apparatus for intraocular injection.

BACKGROUND

An intraocular injection device may be used to administer therapeutic substances to eyes, such as eyes of mammals having eye disorders or diseases.

A number of vision-threatening disorders or diseases of the eye need to deliver a medicament (pharmaceutical, biological, etc.) and/or implantable device to a posterior segment of the eye by intraocular delivery (more specifically intravitreal delivery). One such technique for intraocular delivery is accomplished by intraocular injection into the vitreous body.

A conventional apparatus for intraocular injection may include a pre-filled syringe of a medicament. A conventional pre-filled syringe is supplied with a needle cover in order to maintain sterility of a needle. However, the needle cover is typically frictionally held on the needle which can result in dislodging of the needle cover. If any portion of the needle becomes unsterile prior to use, the syringe must be discarded.

Therefore, there is a need for an apparatus for intraocular injection which ensures that a needle remains covered until use and facilitates removal of a needle cover.

SUMMARY

The exemplary embodiments of the present invention describe an apparatus for intraocular injection which ensures that a needle remains covered until use and facilitates removal of a needle cover.

In an exemplary embodiment, an apparatus for intraocular injection according to the present invention comprises a body adapted to accommodate a syringe having a needle, an outer sleeve telescopically coupled to the body, and at least two arms hingedly coupled to the outer sleeve. Each of the arms comprises a medial portion adapted to encase at least a portion of the needle. When the body moves distally relative to said outer sleeve, the body engages the arms separating the medial portions.

In an exemplary embodiment, the at least two arms are movable apart from each other and together between a first configuration and a second configuration.

In an exemplary embodiment, the at least two arms are adapted to perform a pivoting movement or a sliding movement in radial direction between the first configuration and the second configuration.

In an exemplary embodiment, the at least two arms move apart or together against a biasing mechanism.

In an exemplary embodiment, the medial portions are initially not completely separated and connected by a weak line, plane or three dimensional structure.

In an exemplary embodiment, the body is moveable in longitudinal direction.

In an exemplary embodiment, a distal end of the body applies a force to the at least two arms when the body moves distally relative to the outer sleeve.

In an exemplary embodiment, the arms are sealed in said first configuration.

The person skilled in the art understands that the present invention is not restricted to the explained possibilities.

The above mentioned advantages as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments of the present invention are described herein with reference to the schematic drawings in which:

FIG. 3 depicts a perspective view of an exemplary embodiment of a housing sleeve in a first configuration; and FIG. 4 depicts a perspective view of an exemplary embodiment of a housing sleeve in a second configuration.

DETAILED DESCRIPTION

FIGS. 1 to 4 illustrate an exemplary embodiment of an apparatus for intraocular injection according to the present invention. As shown in the exemplary embodiment of FIG. 1, the apparatus comprises a hollow body 50 which is adapted to accommodate a pre-filled syringe 52 having a needle 54 at its distal end. In the exemplary embodiment, the apparatus may be an auto-injector, delivering the entire contents of the syringe 52 when the apparatus is activated. In another exemplary embodiment, the apparatus may be a reusable, fixed dose delivery device for administering only a portion of the contents of syringe 52 per injection. Those of skill in the art will understand that in another exemplary embodiment the pre-filled syringe 52 may be replaced by a medicament cartridge having a needle or having an interface for engaging a removable needle assembly.

Figure 1:
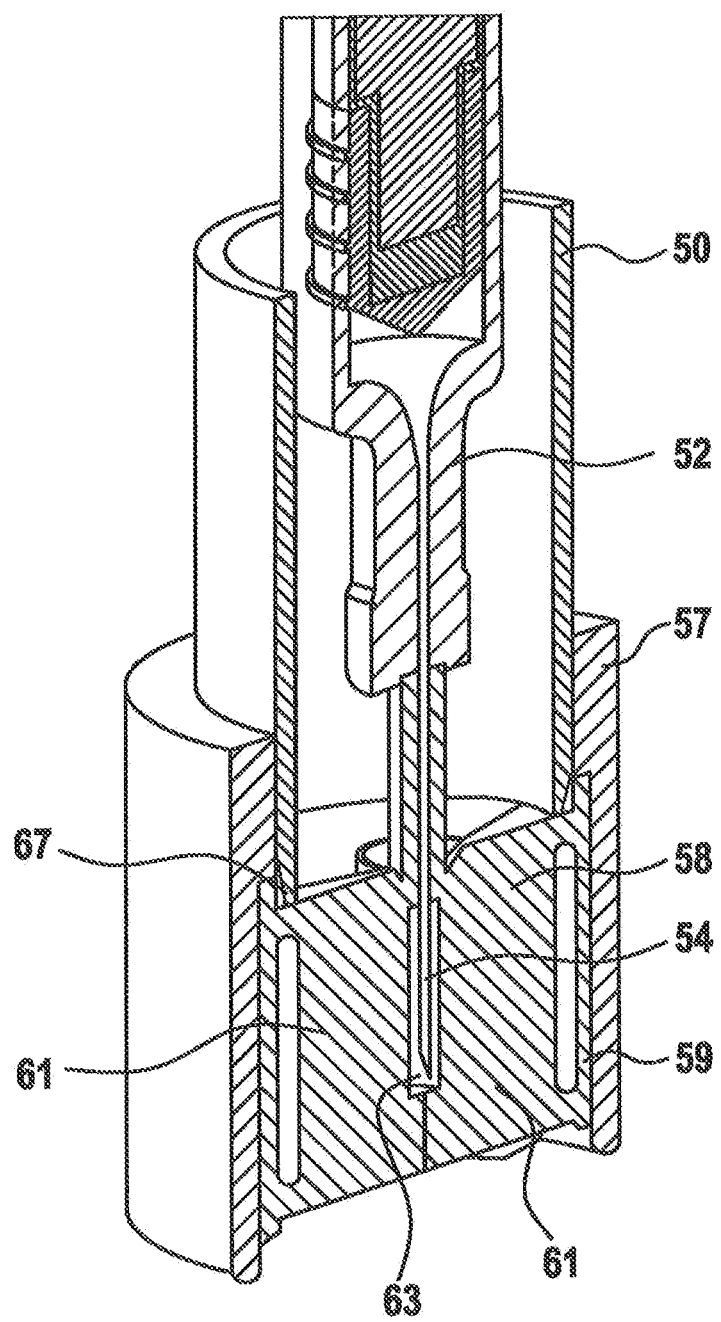
FIG. 1 illustrates a perspective view of a cross section of an exemplary embodiment of an apparatus for intraocular injection in a first configuration.

The body 50 partially fits telescopically within an outer sleeve 57. An inner housing sleeve 58 is coupled to a portion of the outer sleeve 57. In an exemplary embodiment, the inner housing sleeve 58 comprises a shell 59, for example formed as a hollow cylinder, coupled to the outer sleeve 57 and two arms 61 connected to shell 59 at opposite ends (e.g., so as to form a diameter across the shell 59). Each arm 61 has a lateral portion hingedly coupled to the shell 59 (and thereby to the outer sleeve 57) and a medial portion 65 which abuts the medial portion 65 of the other arm 61 when the arms 61 are in a first configuration (as shown in FIGS. 1 and 3). In the exemplary embodiment, the shell 59 and the arms 61 form an integral part but the person skilled in the art understands that alternatively the shell 59 and the arms 61 may be designed as separate parts. In the exemplary embodiment, the arms 61 are biased in the first configuration by, for example, a spring-loaded hinge connection to the shell 59 (and thereby to the outer sleeve 57) or a resilient material providing a hinge-like effect.

In an exemplary embodiment, the inner housing sleeve 58 takes the form of a molded rubber or plastic needle cover, because in the first configuration, the medial portions 65, for example half cylindrical medial portions, of the arms 61 encase the needle 54. As shown in FIG. 1, a notch 63 may be formed in each of the medial portions 65 to provide, in the first configuration, a hole which protects the needle 54.

In an exemplary embodiment, a distal end of the outer sleeve 57 or inner housing sleeve 58 may include a placement foot which is adapted for placement on a target anatomical structure, e.g., the eye. Those of skill in the art will understand that the placement foot of the exemplary embodiments may be made from an at least partially transparent material such that alignment with the eye, e.g. a periphery of the cornea, may be facilitated. Further, those of skill in the art will understand that an underside of the placement foot, for example a surface of the foot which contacts the eye may include a frictional layer or other means for gripping, without injury, the eye.

Figure 2:
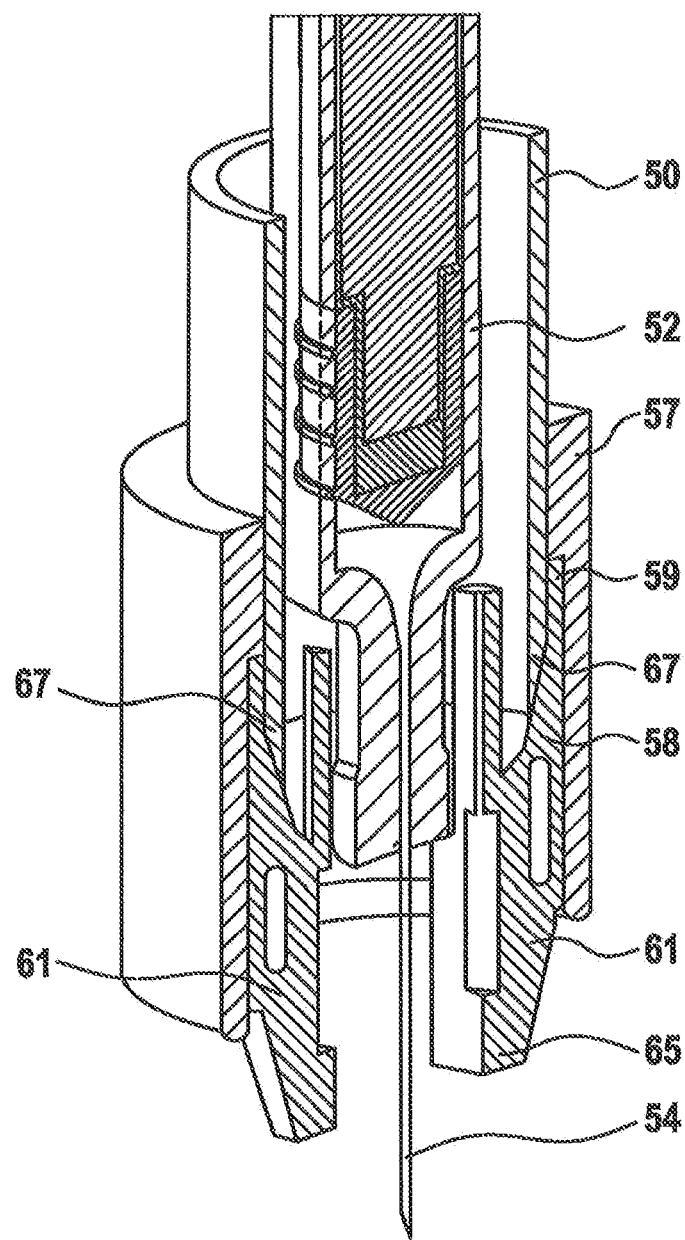
FIG. 2 shows another exemplary embodiment of an apparatus for intraocular in a perspective view of a cross section in a second configuration.

As shown in the exemplary embodiment in FIG. 2, distal movement of the body 50 relative to the outer sleeve 57 causes a distal end 67 of the body 50 to engage and apply a distally directed force on the arms 61. Further distal movement of the body 50 causes the arms 61 and their medial portions 65 to separate into a second configuration by rotating about their respective hinged connections to the shell 59, thereby exposing the needle 54. Those of skill in the art will understand that distal movement of the pre-filled syringe 52 may be synchronized with the movement of the body 50 such that the arms 61 separate and are held apart while the syringe 52 continues with and then completes its travel into distal direction. In this second configuration, the needle 54 projects from the distal end of the apparatus and is therefore accessible for providing an injection into, e.g., the eye.

Thus, this exemplary embodiment of the apparatus provides an automatic means for removing the needle cover prior to the injection.

In an exemplary embodiment, when the needle 54 is withdrawn and the outer body 50 moves proximally relative to the outer sleeve 57, the biasing force on the arms 61 returns the arms 61 return to the first configuration, encasing the needle 54 and preventing needle-stick injury.

FIGS. 3 and 4 show the inner housing sleeve 58 in the first configuration (as in FIG. 1) and in the second configuration (as in FIG. 2) without the other parts of the apparatus or syringe 52.

In another embodiment the inner housing sleeve 58 may be molded such that the arms 61 of this sleeve are initially not completely separated. In this embodiment the downward movement of the body 50 and/or syringe 52 completes the separation of the two arms 61, for example by tearing along specially designed weak planes, as well as moves the two arms 61 apart. The advantage of this embodiment is that protection and sealing of the needle 54 can be more reliably achieved.

Now, using the apparatus within the second configuration the medicament may be administered to the eye.

When the apparatus has been properly placed on the eye, the physician may depress a plunger or similar depressable element coupled to the body 50 and/or the syringe 52 which advances the syringe 52 distally together with the body 50 towards the injection site. Then a medicament may be delivered to the predetermined region of the eye.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An apparatus for intraocular injection comprising:
   a body adapted to accommodate a syringe having a needle;
   an outer sleeve telescopically coupled to the body; and
   at least two arms hingedly coupled to the outer sleeve, each of the arms comprising a medial portion adapted to encase at least a portion of the needle, where the medial portions are initially not completely separated and connected by a weak line, plane or three dimensional structure,
   wherein when the body moves distally relative to said outer sleeve, the body engages the arms separating the medial portions.

2. The apparatus according to claim 1, wherein the at least two arms are movable apart from each other and together between a first configuration and a second configuration.

3. The apparatus according to claim 1, wherein the at least two arms are adapted to perform a pivoting movement or a sliding movement in radial direction between the first configuration and the second configuration.

4. The apparatus according to claim 1, wherein the at least two arms move apart or together against a biasing mechanism.

5. The apparatus according to claim 1, wherein the body is moveable in longitudinal direction.

6. The apparatus according to claim 1, wherein a distal end of the body applies a force to the at least two arms when the body moves distally relative to the outer sleeve.

7. The apparatus according to claim 2, wherein the arms are sealed in said first configuration.

* * * * *